(12) United States Patent
Wu et al.

(10) Patent No.: US 11,941,821 B2
(45) Date of Patent: Mar. 26, 2024

(54) IMAGE SLEEP ANALYSIS METHOD AND SYSTEM THEREOF

(71) Applicant: Yun yun AI Baby camera Co., Ltd., Taipei (TW)

(72) Inventors: Bo-Zong Wu, Taipei (TW); Meng-Ta Chiang, Taipei (TW); Chia-Yu Chen, Taipei (TW); Shih-Yun Shen, Taipei (TW)

(73) Assignee: YUN YUN AI BABY CAMERA CO., LTD., Taipei (TW)

( * ) Notice: Subject to any disclaimer, the term of this patent is extended or adjusted under 35 U.S.C. 154(b) by 522 days.

(21) Appl. No.: 17/138,510

(22) Filed: Dec. 30, 2020

(65) Prior Publication Data

US 2021/0350553 A1 Nov. 11, 2021

(30) Foreign Application Priority Data

May 8, 2020 (TW) .................................. 109115409

(51) Int. Cl.
*G06T 7/246* (2017.01)
*G06V 40/20* (2022.01)
*G10L 25/78* (2013.01)
*G16H 15/00* (2018.01)

(52) U.S. Cl.
CPC .............. *G06T 7/248* (2017.01); *G06V 40/20* (2022.01); *G10L 25/78* (2013.01); *G16H 15/00* (2018.01); *G06T 2207/20081* (2013.01); *G06T 2207/30196* (2013.01); *G06T 2207/30232* (2013.01)

(58) Field of Classification Search
CPC ........... G06T 7/248; G06T 2207/20081; G06T 2207/30196; G06T 2207/30232; G16H 15/00; G06V 40/20; G10L 25/78
See application file for complete search history.

(56) References Cited

U.S. PATENT DOCUMENTS

| 2010/0295783 | A1* | 11/2010 | El Dokor | ................ G06F 3/017 345/158 |
| 2014/0211991 | A1* | 7/2014 | Stoppa | ................... G06V 40/28 382/103 |
| 2020/0074671 | A1* | 3/2020 | Tseng | ........................ G06T 7/73 |
| 2022/0005336 | A1* | 1/2022 | Tanaka | ............... G08B 21/0266 |
| 2022/0028115 | A1* | 1/2022 | Sabripour | ................ G07C 9/37 |

FOREIGN PATENT DOCUMENTS

| CN | 110874560 A | 3/2020 |
| TW | I420424 B | 12/2013 |
| TW | 201727588 A | 8/2017 |
| TW | I642409 B | 12/2018 |

* cited by examiner

*Primary Examiner* — Pinalben Patel
(74) *Attorney, Agent, or Firm* — Muncy, Geissler, Olds & Lowe, P.C.

(57) ABSTRACT

An image sleep analysis method and system thereof are disclosed. During sleep duration, a plurality of visible-light images of a body are obtained. Positions of image differences are determined by comparing the visible-light images. A plurality of features of the visible-light images are identified and positions of the features are determined. According to the positions of the image differences and features, the motion intensities of the features are determined. Therefore, a variation of the motion intensities is analyzed and recorded to provide accurate sleep quality.

21 Claims, 9 Drawing Sheets

IMAGE SLEEP ANALYSIS METHOD AND SYSTEM THEREOF

CROSS-REFERENCE TO RELATED APPLICATIONS

This application is based upon and claims priority under 35 U.S.C. 119 from Taiwan Patent Application No. 109115409 filed on May 8, 2020, which is hereby specifically incorporated herein by this reference thereto.

BACKGROUND OF THE INVENTION

1. Field of the Invention

The present invention is related to a sleep analysis system, and more particularly to an image sleep analysis method and system thereof.

2. Description of the Prior Arts

Taiwan patent No. 1420424 proposes a baby sleep monitoring system and method to monitor the baby's sleep status. The monitoring system has a cellphone with a camera and an accelerator mounted on the baby's bed to detect the shaking status of the bed. If the bed is shaking, the cellphone takes a picture of the baby on the bed by the camera thereof. The cellphone further determines whether the baby's eyes open by image analyzing. When the baby's eye opens, the cellphone transmits an awake notification.

Taiwan patent No. 1642409 proposes a sleep analysis method. A body to be analyzed has to wear an electrical device having a three-axis accelerometer, such as a smartwatch. The three-axis accelerometer detects the body's motions in sleep, so the sleep analysis method determines the quality of sleep for the body by analyzing the motions.

Based on the foregoing description, the accelerator or three-axis accelerometer etc. detector is required in the present sleep analysis device to monitor the sleep status of the baby or adult and simply transmit notification and analysis result.

To overcome the shortcomings, the present invention provides an image sleep analysis method and system thereof to mitigate or to obviate the aforementioned problems.

SUMMARY OF THE INVENTION

An objective of the present invention is to provide an image sleep analysis method and system thereof.

To achieve the objective as mentioned above, the image sleep analysis method has following steps:
(a) obtaining a plurality of visible-light images of a body to be monitored;
(b) comparing the visible-light images to determine a plurality of image differences among the visible-light images and determining a first image position of each of the image differences;
(c) identifying a plurality of features of each of the visible-light images and determining a second image position of each of the features;
(d) determining a motion intensity of each of the features according to the first image positions of the image differences and the second image positions of the features; and
(e) recording and analyzing a variation of the motion intensities.

With the foregoing description, in the image sleep analysis method of the present invention, real-time visible-light images of the body are obtained during sleep duration. To increase an accuracy of determining the motion intensity of the body, the image differences are determined by comparing the continuously-obtained visible-light images, the features, such as head, hands, feet, or the like, of the visible-light images are identified, and the variation of the motion intensities of the body is determined according to the motion intensities of each of the at least one feature. Therefore, the present invention does not require any wearable motion sensor for the body to be monitored. In addition, the present invention provides more details for sleep information.

To achieve the objective as mentioned above, the image sleep analysis system has:
a visible-light sensor outputting a plurality of visible-light images of a body;
a processing unit electrically connected to the visible-light sensor to obtain the visible-light images during sleep duration, identifying a plurality of features, monitoring a variation of motion intensities of the features, and analyzing the variation of motion intensities of the features to generate a sleep quality report;
a first communication module electrically connected to the processing unit; and
a display device linking to the first communication module to obtain the sleep quality report and displaying the sleep quality report.

With the foregoing description, the image sleep analysis system is mounted on a bedside and the visible-light sensor aligns the bed to sense the visible-light images of the body on the bed. The processing unit obtains the visible-light images from the visible-light sensor and further identifies the at least one feature, such as head, hands, feet, or the like of the visible-light images to monitor and analyze the variation of the motion intensities of the body. Therefore, the present invention does not require any wearable motion sensor for the body to provide more details for sleep information by accurately real-time monitoring of the body's motion. In addition, the sleep information is directly displayed on the display device.

Other objectives, advantages and novel features of the invention will become more apparent from the following detailed description when taken in conjunction with the accompanying drawings.

DETAILED DESCRIPTION OF THE PREFERRED EMBODIMENTS

With multiple embodiments and drawings thereof, the features of the present invention are described in detail as follows.

Figure 1:
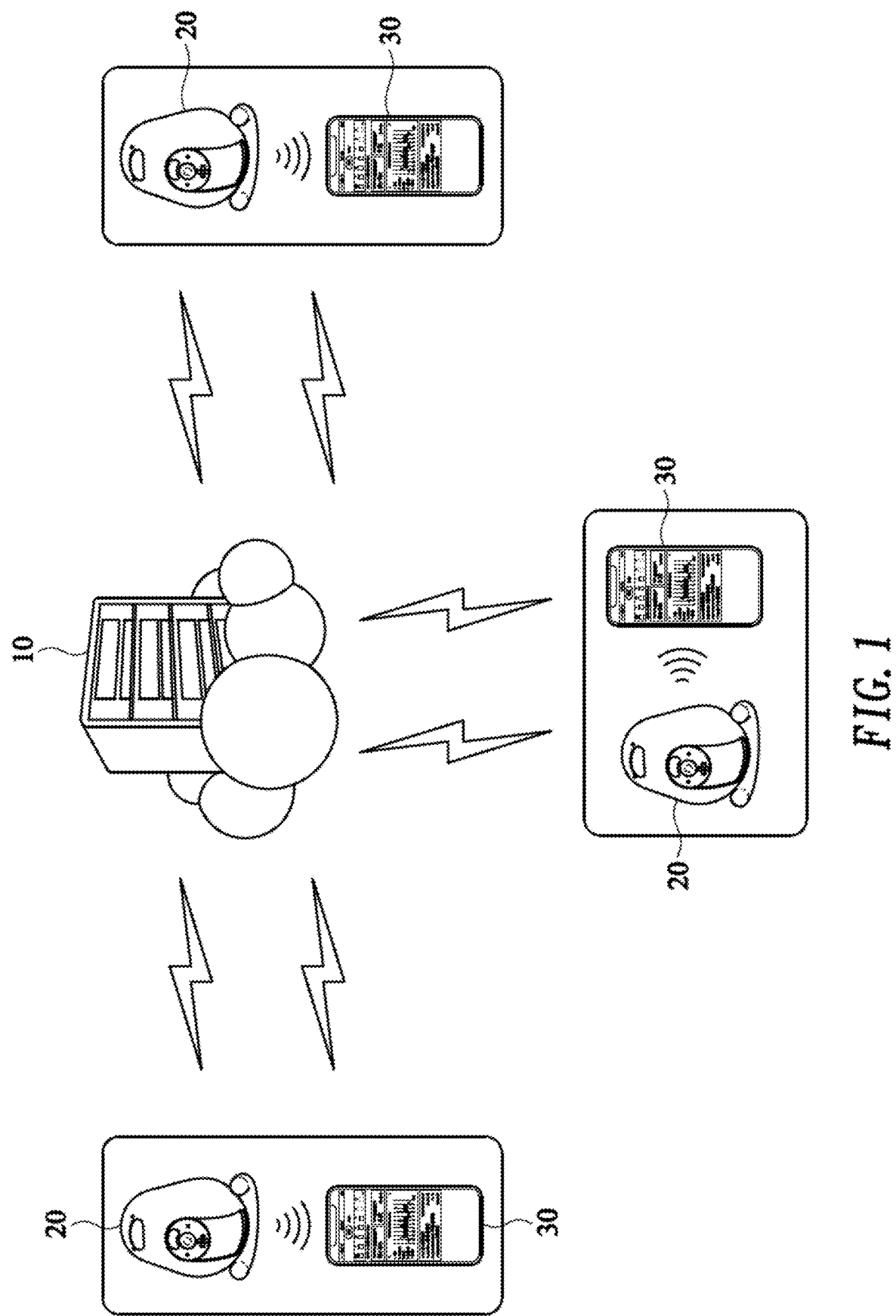
FIG. 1 is a schematic view of a first embodiment of an image sleep analysis system in accordance with the present invention.

With reference to FIG. 1, an image sleep analysis system 1 of the present invention has a cloud server 100, a plurality of cameras 20 and a plurality of portable display device 30. The cloud server links to each camera 20 and each portable display device 30 and each camera 20 also links to the corresponding portable display device 30. The cloud server 10 provides a plurality of user accounts for different users and the user can log into the cloud server 10 through the camera 20 and portable display device 30. In one embodiment, the portable display device 30 may be a smartphone.

Figure 2:
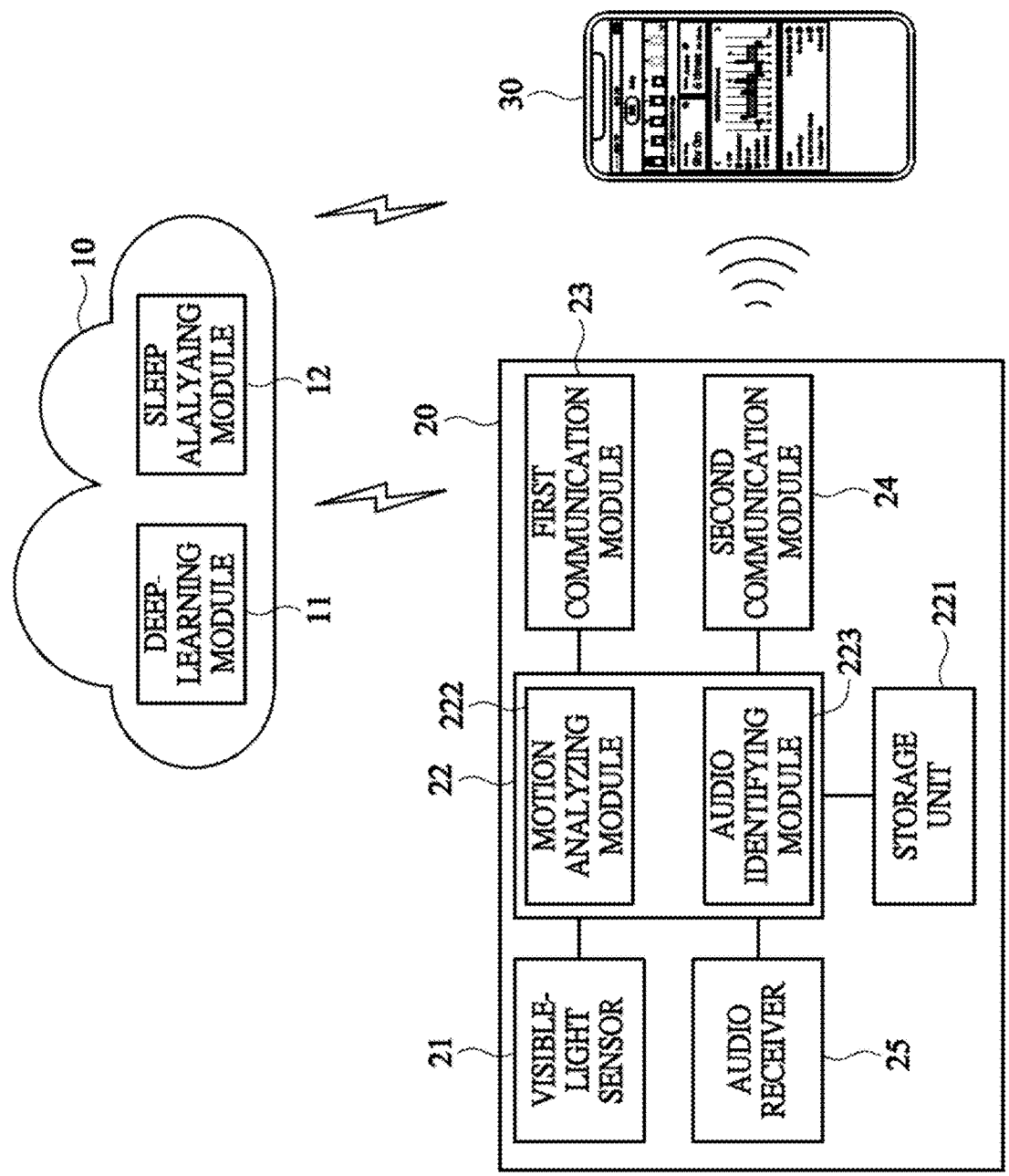
FIG. 2 is a schematic view of a second embodiment of an image sleep analysis system in accordance with the present invention.

With further reference to FIG. 2, the camera 20 has a visible-light sensor 21, a processing unit 22, a storage unit 221, a first communication module 23, a second communication module 24 and an audio receiver 25. The processing unit 22 is electrically connected to the visible-light sensor 21, the storage unit 221, the first communication module 23, the second communication module 24 and the audio receiver 25. The processing unit 22 links to the cloud server 10 through the first communication module 23 and links to the portable display device 30 through the second communication module 30.

Figure 3:
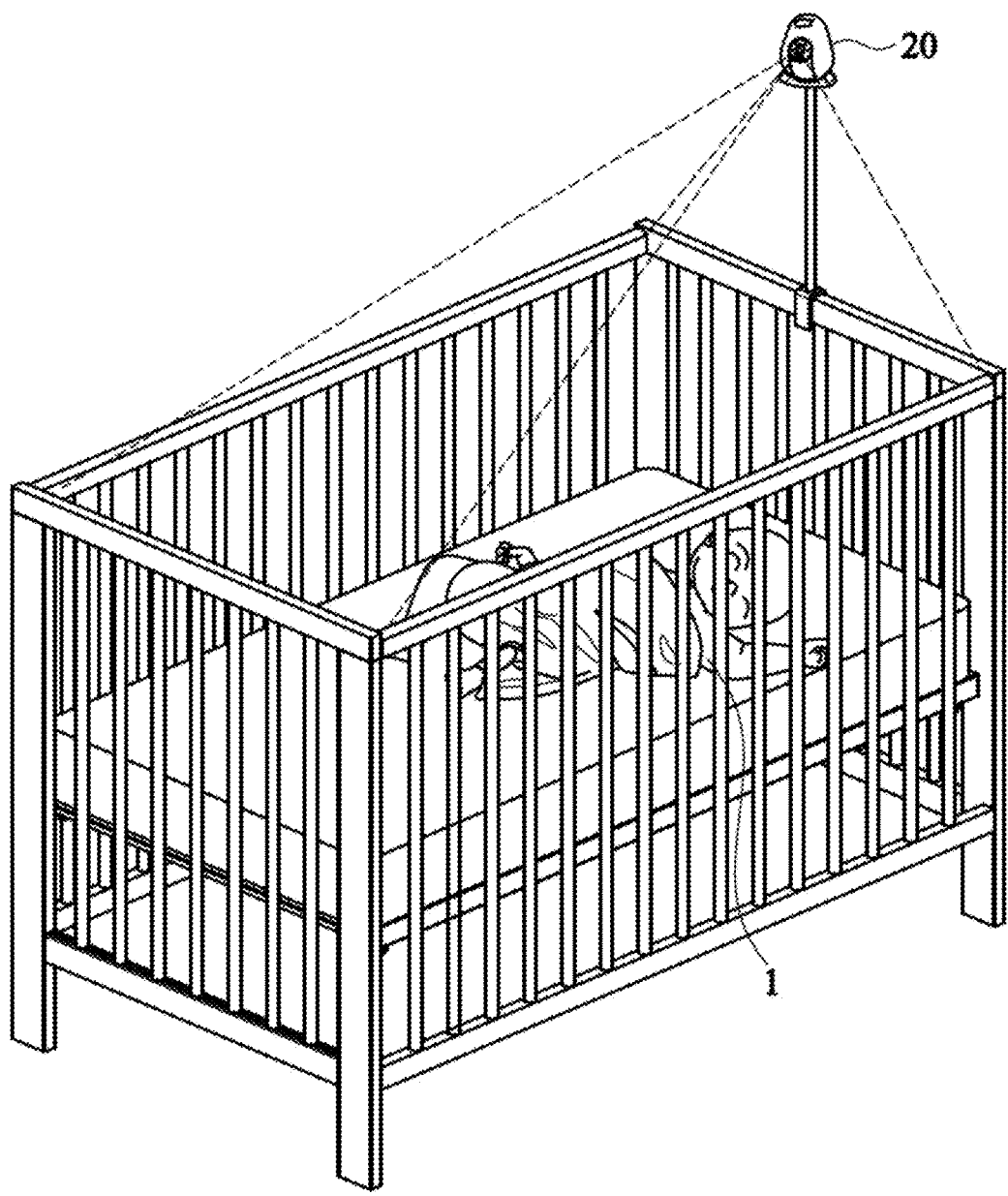
FIG. 3 is a schematic view of the image sleep analysis system mounted on a bedside in accordance with the present invention.
Figure 4:
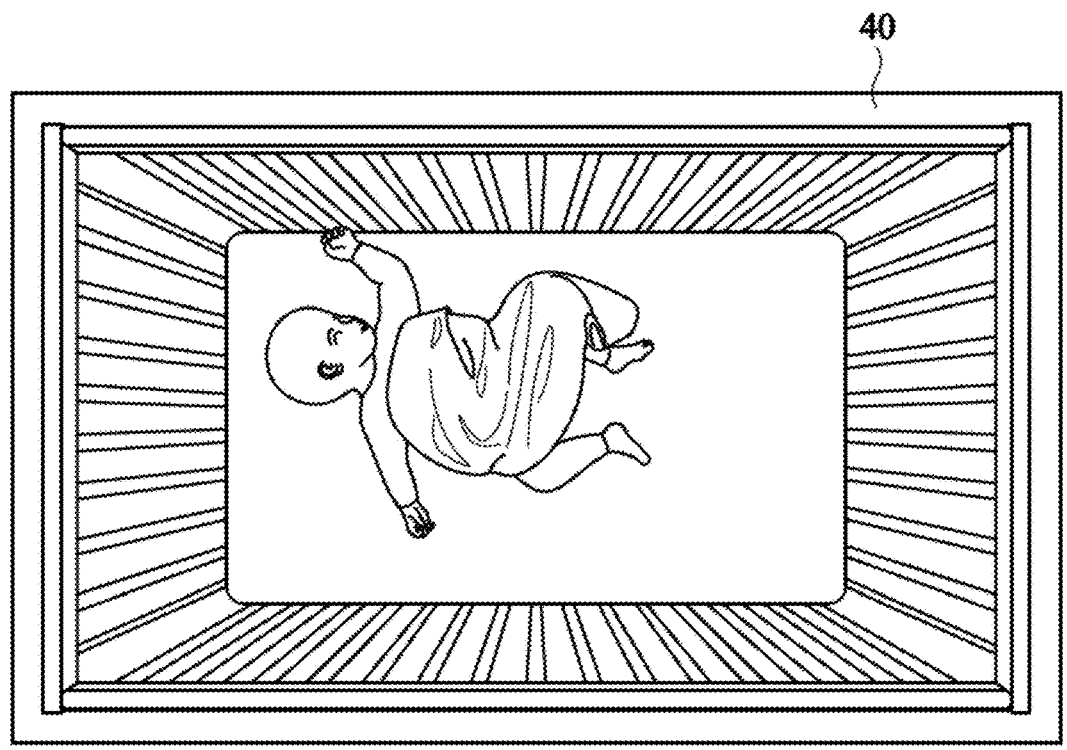
FIG. 4 is a schematic view of one image sensed by a visible-light image of the image sleep analysis system mounted on a bedside in accordance with the present invention.

With further reference to FIG. 3, the camera 20 is mounted on one bedside. Using a baby bed as an example, a sensing range of the visible-light sensor 21 of the camera 20 covers the baby bed and a whole body 1 of a baby on the bed is sensed by the visible-light sensor 21. The processing unit 22 continuously receives a plurality of the visible-light images 40 of the baby on the bed, as shown in FIG. 4. The processing unit 22 is electrically connected to the audio receiver 25 to receive an audio signal around the audio receiver 25.

With reference to FIG. 2, a motion analyzing module 222 and an audio identifying module 223 are built into the processing unit 22. A deep-learning module 11 and a sleep analyzing module 12 are built into the cloud server 10. If the processing unit 22 employs an AI smart processor with high-performance computing, the deep-learning module 11 and the sleep analyzing module 12 may be built into the processing unit 22.

Figure 5:
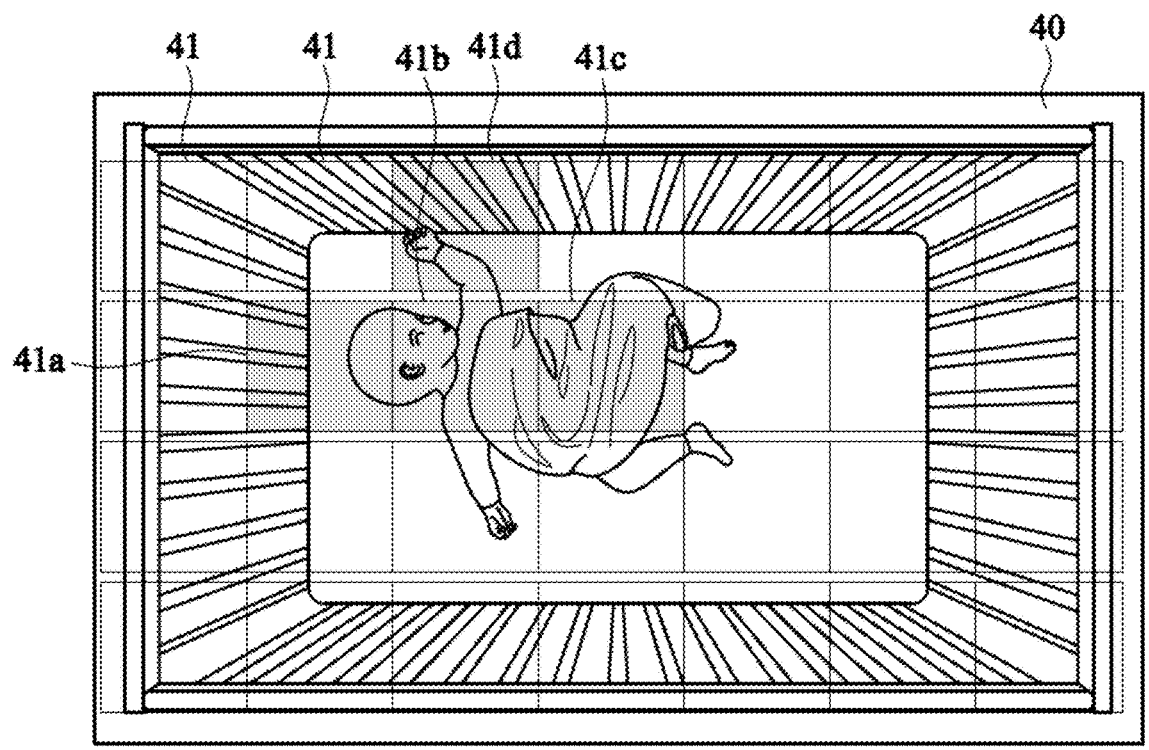
FIG. 5 is a schematic view of the image divided into a plurality of sub-images in accordance with the present invention.

With reference to FIGS. 2, 4 and 5, the processing unit 22 continuously receives a plurality of visible-light images 40 and compares the visible-light images 40 to determine a plurality of image differences between the visible-light images 40 and an image position of each image difference. In particular, the motion analyzing module 222 divides the visible-light image into sub-images and then compares whether the image difference between the same sub-image 41 in the previous and present images 40 exceeds a difference threshold. If so, the image difference between the sub-images is obvious and the sub-images are marked. As shown in FIG. 5, the four sub-images 41a, 41b, 41c, 41d are easily determined to be marked since the four sub-images 41a, 41b, 41c, 41d correspond to head, hand, and trunk of the body. In FIG. 5, the four sub-images are marked in gray.

Figure 6:
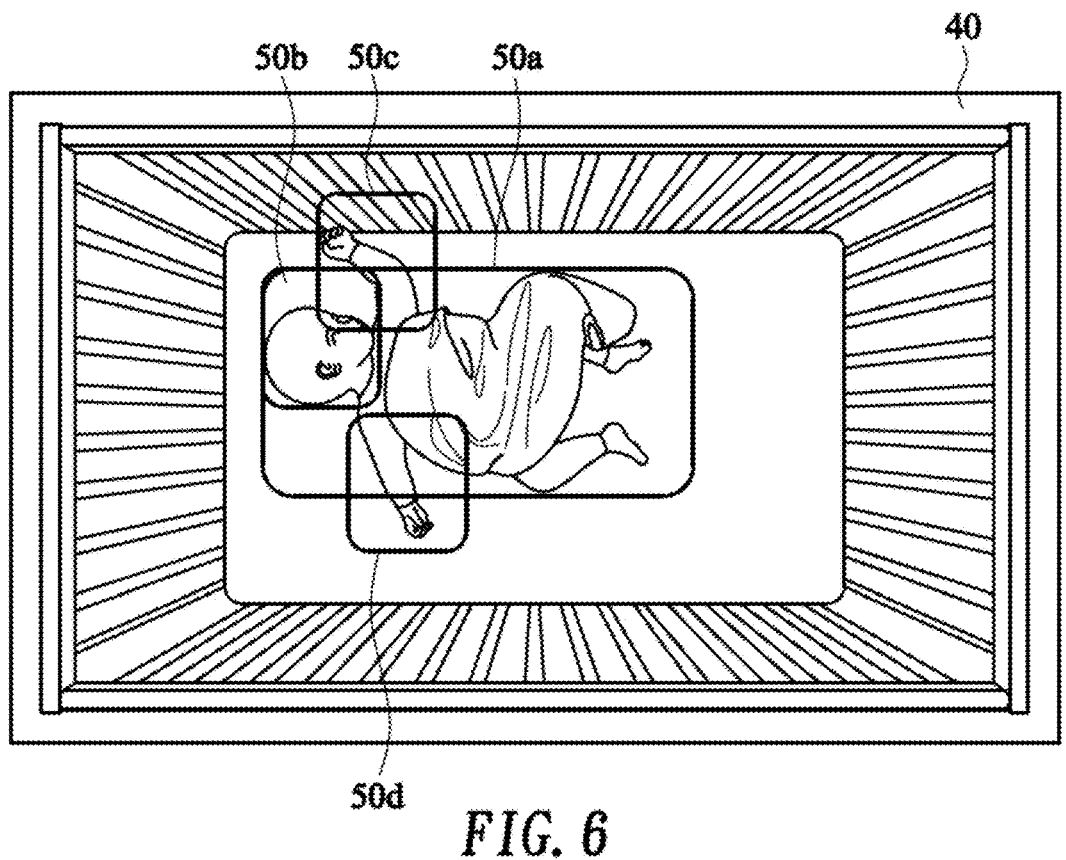
FIG. 6 is a schematic view of one image on which a plurality of features is marked in accordance with the present invention.
Figure 7:
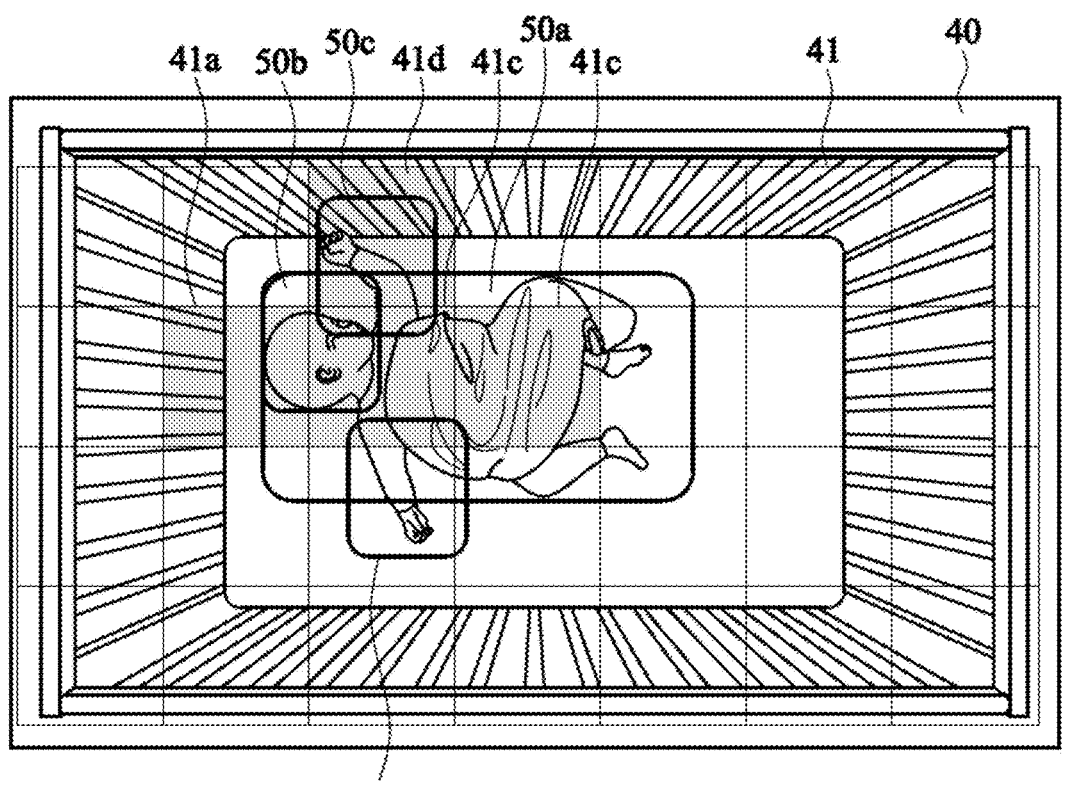
FIG. 7 is a schematic view of one image combined the images of FIGS. 5 and 6.

At the same time, the processing unit 22 transmits the received visible-light images to the cloud server 10 through the first communication module 23. Since the camera 20 has logged into the cloud server 10 by identifying the registered account, the visible-light images are stored in a cloud storage space for the corresponding account of the camera 20. The deep-learning module 11 of the cloud server 10 identifies different features 50a, 50b, 50c and 50d of the visible-light images 40. Since the deep-learning module has learned and stored a sleep posture learning model, the deep-learning module 11 of the cloud server 10 identifies different features 50a, 50b, 50c and 50d of the visible-light images according to the sleep posture learning model and the image positions thereof. As shown in FIG. 6, in the present embodiment, the features include face, hands, trunk and may be include feet or the like part of the body.

When the cloud server 10 completes identification of the different features 50a, 50b, 50c and 50d and the image positions thereof, these identified information are transmitted backwardly to the processing unit 22 through the first communication module 23. Therefore, the processing unit 22 has stored the marked sub-images and the image positions thereof, and the features 50a, 50b, 50c and 50d and the positions thereof, the processing unit 22. As shown in FIGS. 5 and 6, the processing unit 22 reads the marked sub-images 41a, 41b, 41c and 41d and the image positions thereof, the features 50a, 50b, 50c and 50d and the image positions thereof to determine a plurality of overlapped areas between the features 50a, 50b, 50c and 50d (hereinafter the first to fourth features 50a, 50b, 50c and 50d) and the corresponding sub-images 41a, 41b, 41c and 41d (hereinafter the first to fourth sub-images 41a, 41b, 41c and 41d). If the overlapped area between a first feature and a first sub-image corresponding the first feature exceeds a first area threshold, a motion intensity value of the first feature is set to a first motion intensity value. On the contrary, the motion intensity value of the first feature is given a second motion intensity value. As shown in FIG. 6, the four sub-images 41 are marked in the visible-light image 40. The first to fourth overlapped areas between the first to fourth sub-images and the first to fourth features from high to low are the third overlapped area, the second overlapped area, the fourth overlapped area and the first overlapped area. All the overlapped areas are respectively further compared with the first area threshold. The second and third overlapped areas are larger than the first area threshold, so the motion intensity values of the second and third features are respectively set to the first motion intensity value a1. The first and fourth overlapped areas are further compared with the second area threshold. The fourth overlapped area is larger than the second area threshold and the first overlapped area is less than the second area threshold. The motion intensity value of the fourth feature is set to the second motion intensity value a2 and the motion intensity value of the first feature is set to "0". In another embodiment, more area thresholds may be used.

To accurately determine the motion intensity of the body, after the processing unit 22 continuously transmits the motion intensity values of the features to the cloud server 10, the sleep analyzing module 12 of the cloud server 10 further periodically reads the motion intensity values of the features to calculate standard deviations to obtain the motion intensity value of each feature for each period. For example, if the motion intensity values of the head and trunk are a2, the motion intensity value of the left hand is a1 and the motion intensity value of the right hand is "0", different weights are given to the different features. For example, a weight of the head is 60%, a weight of the trunk is 30% and a weight of the hand is 10%. A movement of the body in one minute is calculated by summing the products of the motion intensity values and the corresponding weights (a2*60%+a2*30%+a1*10%+0*10%).

In addition, the deep-learning module 11 of the cloud server 10 may previously learn and store a caregiver posture learning model to identify a feature of the caregiver's body from the visible-light images and to record identifying time. If the camera 20 is used in a baby sleep analysis application, the deep-learning module 11 transmits the feature of the caregiver's body and the identifying time backwardly to the processing unit 22. The processing unit 22 may further have an audio identifying module 222. The audio identifying module 223 has a crying learning model to identify a crying feature from the audio signal and record an identifying time.

Figure 8:
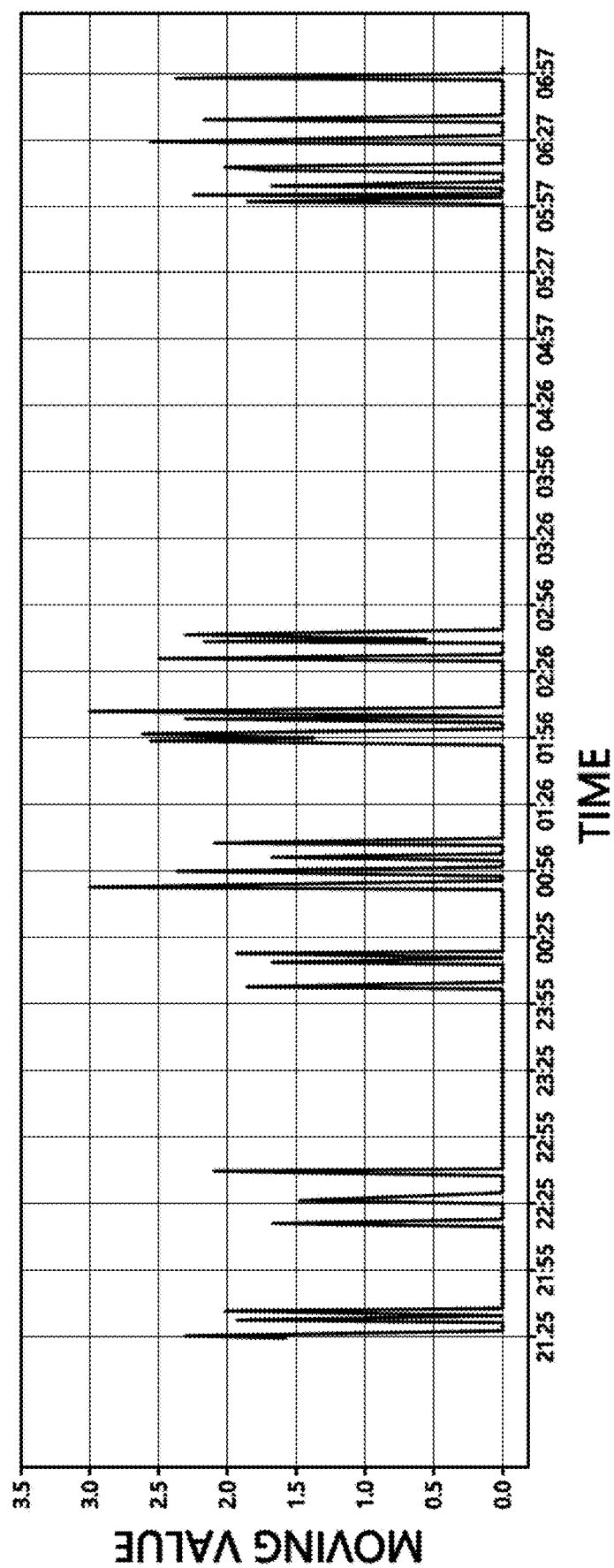
FIG. 8 is a graph showing a variation of motion intensities in accordance with the present invention.
Figure 9:
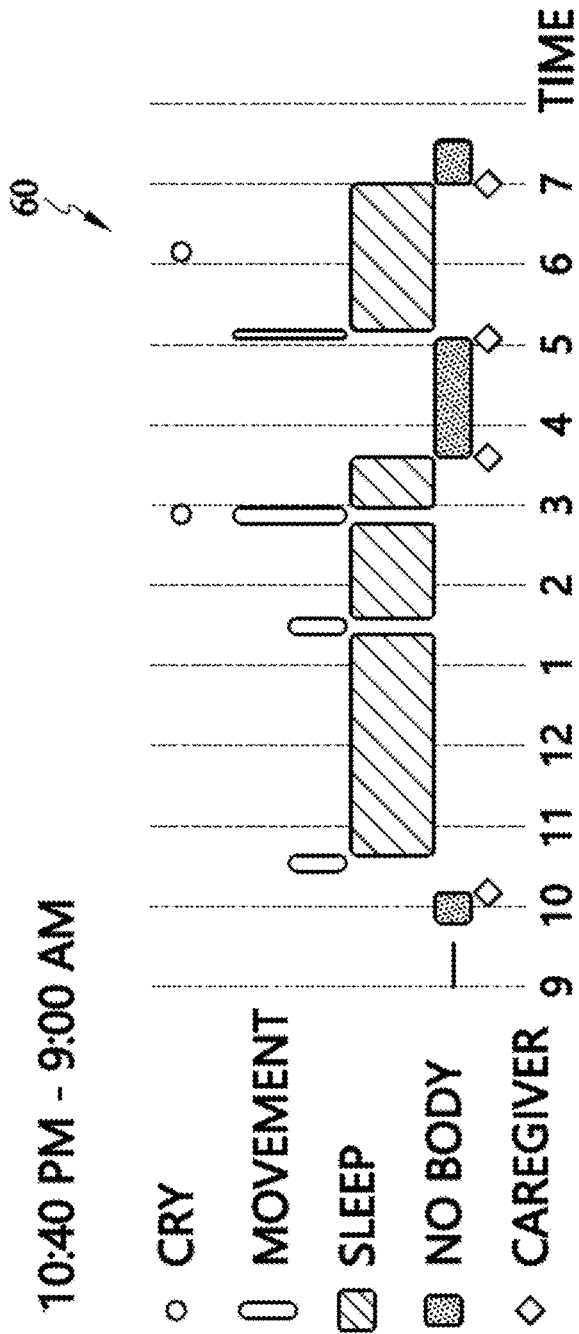
FIG. 9 is a sleep analysis graph in accordance with the present invention.
Figure 10:
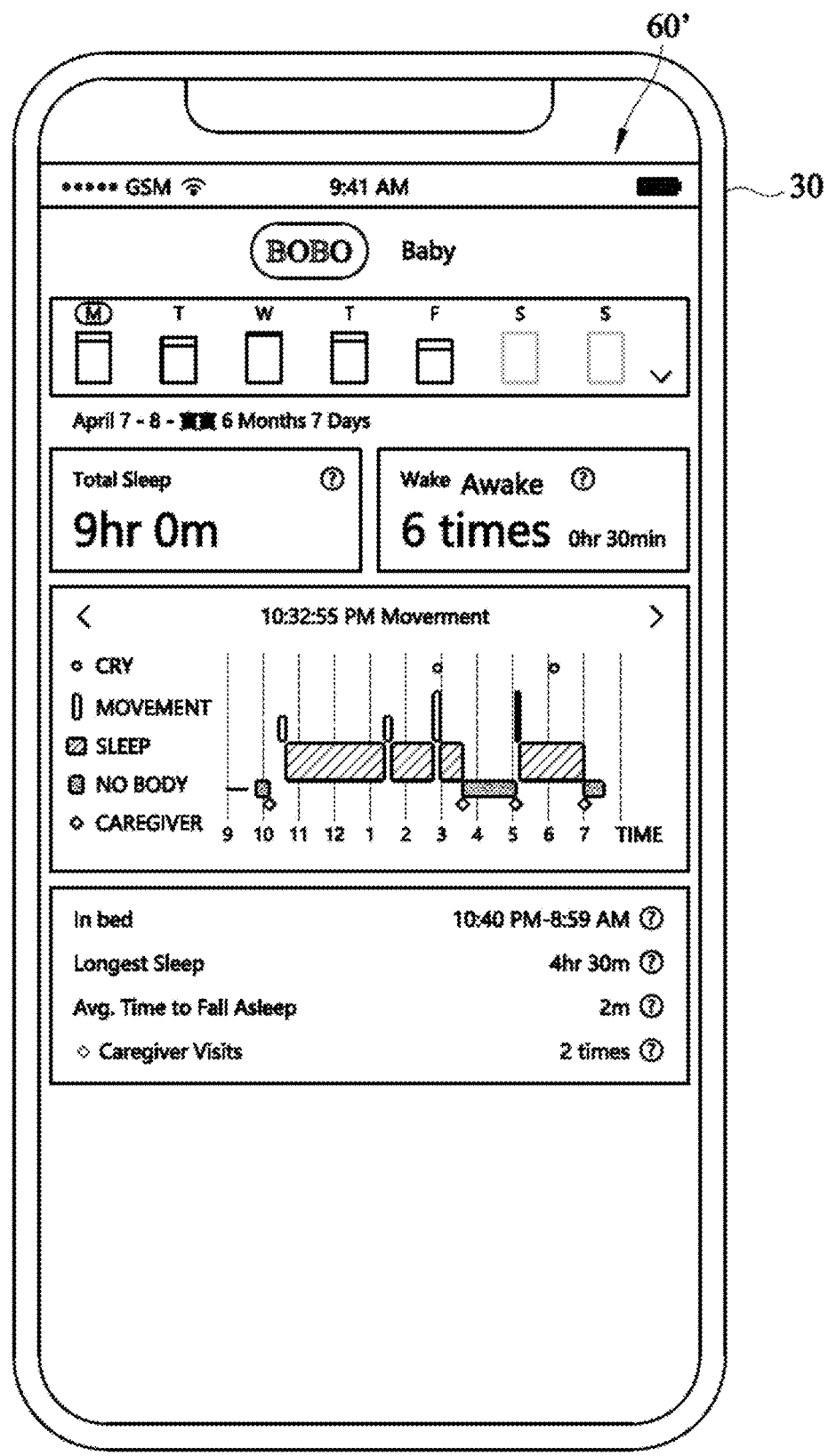
FIG. 10 is a sleep quality report shown on the display device in accordance with the present invention.

Therefore, using the camera 20 and the cloud server 10 real-time to monitor the asleep body during sleep duration obtains a variation of the movements of the body (motion intensity variation) as shown in FIG. 8. The sleep analyzing model 12 of the cloud server 10 further analyzes the variation of the movements to generate a sleep quality report 60. As shown in FIG. 9, the movements and moving times thereof recorded in the sleep duration (10:40 PM to 9:00 AM) of every day are obtained. If anyone of the movements exceeds a light-sleep threshold, the movements are marked and times of marking the movements are defined as time stamps. According to the time stamps, a plurality of sleep zones of the sleep duration is defined and a time length of each sleep zone is calculated. According to the time lengths, a sleep quality of the body is calculated every day. With reference to FIG. 10, the sleep analyzing module 12 may calculate total sleep time, an average sleep time, a longest sleep time, awaking time and frequency thereof, crying time, times of taking care etc. related sleep information and generates the sleep quality report including this sleep information 60' every day.

When the present invention is used in the baby application, the parents obtain the baby's real sleep information and further understand the baby's sleeping habits, avoid taking care of the baby during the sleeping duration and try to adjust to take care of the baby during awaking duration. Therefore, the parents can strengthen the baby's long-term sleep training and get more times to rest by themselves.

Figure 11:
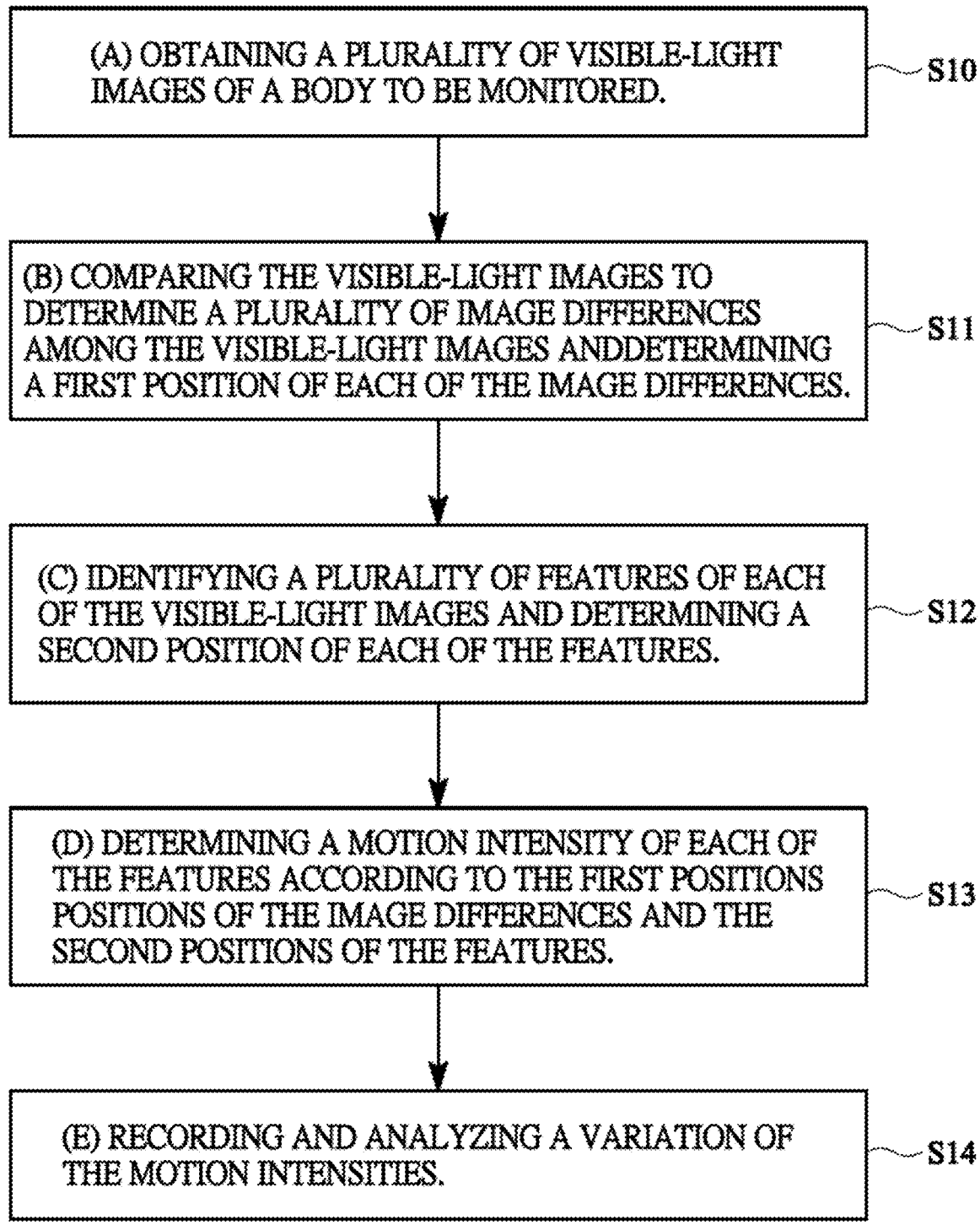
FIG. 11 is a flow chart of an image sleep analysis method in accordance with the present invention.

Based on the foregoing the image sleep analysis system, the image sleep analysis method of the present invention has following steps (a) to step (e), as shown in FIG. 11.

In the step (a), a plurality of visible-light images is obtained in a sleep duration S11.

In the step (b), the visible-light images are compared to identify image differences and determine image positions of the image differences S11. In the present embodiment, pixels of the previous visible-light image are compared with the pixels of the present visible-light image to determine whether the same pixel has changed. Therefore, the image position of each image difference may be coordinates of pixels.

In the step (c), a plurality of features is identified from the visible-light images and image positions of the features are determined S12. In the present embodiment, the features may include head, hands, trunk etc. body's parts. Using an AI deep-learning technology with a sleep posture learning model identifies the features from each visible-light image and determines image positions of the features.

In the step (d), according to the image positions of the image differences and the image positions of the features, a motion intensity of each feature is determined S13. In the present embodiment, the motion intensity of each feature is determined by calculating overlapped areas between the image differences and the corresponding features. If the overlapped area between the image difference and the corresponding feature is larger, the motion intensity of the feature is high. If the overlapped area between the image difference and the corresponding feature is smaller, the motion intensity of the feature is low. In particular, the visible-light image is divided into a plurality of sub-images. Comparing the same sub-images of the previous visible-light image and the present visible-light image determines whether an amount of the changed pixels of the sub-image exceeds a difference threshold. If so, the sub-images are marked. The overlapped area between the marked sub-image and the corresponding feature is further calculated. One or more area thresholds may be preset to compare with each of the overlapped areas. According to the comparison result, a motion intensity value is given to the corresponding feature. To accurately determine the motion intensity of the body, the visible-light images and the motion intensity values of the features are periodically obtained. After calculating a highest value, an average, or a standard deviation from the motion intensity values of the same feature in one period, a single motion intensity value of each feature in one period is obtained. And then, a movement of the body in one period is calculated by summing products of the motion intensity values and corresponding weights of the features.

In the step (e), a variation of the motion intensity is analyzed and recorded S14. In the present embodiment, the movements and moving times thereof recorded in the sleep duration of every day are obtained. If anyone of the movements exceeds a light-sleep threshold, the movements are marked and times of marking the movements are defined as time stamps. According to the timestamps, a plurality of sleep zones of the sleep duration is defined and a time length of each sleep zone is calculated. According to the time lengths, a sleep quality of the body for one day is calculated. The sleep quality at least has a total sleep time, an average sleep time, a longest sleep time, waking time and frequency thereof and a crying time, time of taking care etc. related sleep information may be included in the sleep quality for baby sleep analysis monitor application.

Based on the foregoing description, in the image sleep analysis method of the present invention, real-time visible-light images of the body are obtained during sleep duration. To increase an accuracy of determining the motion intensity of the body, the image differences are determined by comparing the continuously-obtained visible-light images, the features, such as head, hands, feet, or the like, of the visible-light images are identified, and the variation of the motion intensities of the body is determined according to the motion intensities of each of the at least one feature. Therefore, the present invention does not require any wearable motion sensor for the body to be monitored. In addition, the present invention provides more details for sleep information. When the present invention is used in the baby sleep analysis application, more baby's sleep details are obtained so the parents can strengthen the baby's long-term sleep training and get more times to rest by themselves.

Even though numerous characteristics and advantages of the present invention have been set forth in the foregoing description, together with the details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An image sleep analysis method, comprising steps of:
   (a) obtaining a plurality of visible-light images of a body to be monitored;
   (b) comparing the visible-light images to determine a plurality of image differences among the visible-light images and determining a first image position of each of the image differences;
   (c) identifying a plurality of features of each of the visible-light images and determining a second image position of each of the features;
   (d) determining a motion intensity of each of the features according to the first image positions of the image differences and the second image positions of the features; and
   (e) recording and analyzing a variation of the motion intensities.

2. The image sleep analysis method as claimed in claim 1, wherein in the step (d), the motion intensity of each feature is determined by an overlapped area between the feature and the corresponding image difference thereof, wherein if the overlapped area is larger, the motion intensity of the feature is higher and if the overlapped area is smaller, the motion intensity of the feature is lower.

3. The image sleep analysis method as claimed in claim 2, wherein the step (b) comprising steps of:
   (b1) dividing each visible-light image into a plurality of sub-images;
   (b2) determining whether the image difference between the same sub-images of the previous visible-light image and the present visible-light image exceeds a difference threshold; and
   (b3) marking and recording the sub-image of the step (b2) if a determining result of the step (b2) is positive.

4. The image sleep analysis method as claimed in claim 3, wherein the step (c) comprising steps of:
   (c1) reading a sleep posture learning model; and
   (c2) identifying the features of each visible-light image and determining the second image positions of the features.

5. The image sleep analysis method as claimed in claim 4, wherein the step (d) comprising steps of:
   (d1) reading the first image position of each marked sub-image and the second image positions of the corresponding feature; and
   (d2) determining the overlapped area between the marked sub-image and the corresponding feature; wherein if the overlapped area is larger than a first area threshold, the motion intensity of the feature is set to a first motion intensity value; and if the overlapped area is smaller than the first area threshold, the motion intensity of the feature is set to a second motion intensity value.

6. The image sleep analysis method as claimed in claim 5, wherein in the step (d2), if the overlapped area is smaller than the first area threshold, the overlapped area is further compared with a second area threshold, wherein if the overlapped area is smaller than the second area threshold, the motion intensity of the feature is reset to a third motion intensity value.

7. The image sleep analysis method as claimed in claim 6, wherein the step (d) further comprises a step of (d3) and in the step of (d3), a movement of the body in a preset duration is calculated by the motion intensity values periodically obtained in the preset duration.

8. The image sleep analysis method as claimed in claim 7, wherein the step (d3) further comprises steps of:
   (d31) giving different weights to different features;
   (d32) in each preset duration, the movement of the body is determined by summing products of the motion intensity values and the corresponding weights.

9. The image sleep analysis method as claimed in claim 8, wherein in the step (d32), a largest motion intensity value, an average motion intensity value or a standard deviation of the motion intensities of each feature is determined as a single motion intensity of the corresponding feature; and the movement of the body is determined by summing products of the single motion intensity values and the corresponding weights.

10. The image sleep analysis method as claimed in claim 8, wherein the step (e) comprises:
    (e1) obtaining the movements and moving times thereof recorded in the sleep duration of every day;
    (e2) marking the movements which exceed a light-sleep threshold and defining times of marking the movements as timestamps;
    (e3) according to the timestamps, defining a plurality of sleep zones of the sleep duration;
    (e4) calculating a time length of each sleep zone; and
    (e5) according to the time lengths, analyzing a sleep quality of the body.

11. The image sleep analysis method as claimed in claim 10, wherein in the step (e5), the sleep quality has a total sleep time, an average sleep time and a longest sleep time.

12. The image sleep analysis method as claimed in claim 11, wherein in the step (c), the features have baby's body features and caregiver's body features, wherein:
    in the step (c1), the sleep posture learning model is a baby sleep posture learning model; and
    the step (c) further comprises steps of:
      (c3) reading a caregiver sleep posture learning model; and
      (c4) according to the caregiver sleep posture learning model, identifying the features of the caregiver' body from each visible-light image and an identifying time.

13. The image sleep analysis method as claimed in claim 12, wherein the step (e5) further calculates time length of taking care and frequency thereof.

14. The image sleep analysis method as claimed in claim 12, wherein
    the step (a) further obtains an audio signal; and
    the step (c) further comprises steps of:
      (c5) reading a crying learning model; and
      (c6) according to the crying learning model, identifying an audio feature of the audio signal, and recording an identifying time.

15. An image sleep analysis system, comprising:
    a visible-light sensor outputting a plurality of visible-light images of a body;
    a processing unit electrically connected to the visible-light sensor to perform following steps of:
    (a) obtaining the visible-light images during sleep duration;
    (b) comparing the visible-light images to determine a plurality of image differences among the visible-light images and determining a first image position of each of the image differences;

(c) identifying a plurality of features of each of the visible-light images and determining a second image position of each of the features;
(d) determining a motion intensity of each of the features according to the first image positions of the image differences and the second image positions of the features; and
(e) monitoring a variation of motion intensities of the features, and analyzing the variation of motion intensities of the features to generate a sleep quality report;
a first communication module electrically connected to the processing unit; and
a display device linking to the first communication module to obtain the sleep quality report and displaying the sleep quality report.

16. The image sleep analysis system as claimed in claim 15, wherein the sleep quality report displayed on the display device has a total sleep time, an average sleep time and a longest sleep time.

17. The image sleep analysis system as claimed in claim 16, wherein
the processing unit identifies the features has a plurality of baby's body features and a plurality of caregiver's body features; and
the sleep quality report has a baby's total sleep time, a baby's average sleep time, a baby's longest sleep time, a time length of taking care and frequency of taking care.

18. The image sleep analysis system as claimed in claim 17, further comprises an audio receiver electrically connected to the processing unit, wherein during sleep duration, the processing unit obtains the audio signal, identifies a crying feature of the audio signal and an identifying time, and adds the crying time into the sleep quality report.

19. The image sleep analysis system as claimed in claim 15, further comprising:
a second communication module electrically connected to the processing unit;
a cloud server linking to the processing unit through the second communication module, wherein the processing unit transmits the visible-light images to the cloud server; the cloud server identifies the features of each visible-light image, determines a second image positions of the features and transmits the features and the second image positions to the processing unit; the processing unit determines a plurality of motion intensities of the features and transmits the motion intensities to the cloud server; and the cloud server analyzes the motion intensities of the features and generates the sleep quality report.

20. The image sleep analysis system as claimed in claim 19, wherein the display device links to the cloud server to download and display the sleep quality report.

21. The image sleep analysis system as claimed in claim 20, wherein the processing unit determines the motion intensity of each feature by an overlapped area between the feature and the corresponding image difference thereof according to the first image positions and the second image positions, wherein
if the overlapped area is larger, the motion intensity of the feature is higher; and
if the overlapped area is smaller, the motion intensity of the feature is lower.

* * * * *